US00PP17169P3

(12) United States Plant Patent
Dirr

(10) Patent No.: US PP17,169 P3
(45) Date of Patent: Oct. 24, 2006

(54) ***HYDRANGEA MACROPHYLLA* PLANT NAMED 'BLUSHING BRIDE'**

(50) Latin Name: *Hydrangea macrophylla*
Varietal Denomination: Blushing Bride

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 24 days.

(21) Appl. No.: 11/080,137

(22) Filed: Mar. 15, 2005

(65) Prior Publication Data

US 2006/0212982 P1 Sep. 21, 2006

(51) Int. Cl.
*A01H 5/00* (2006.01)

(52) U.S. Cl. ..... Plt./250

(58) Field of Classification Search ..... Plt./250
See application file for complete search history.

(56) References Cited

PUBLICATIONS

Dirr, M.A. "*Hydrangea macrophylla* (Thunberg ex J.A. Murray) Seringe" (2004) *Hydrangeas for American gardens*; Published by Timber Press, Portland, Or. Chapt. 7, pp. 71–115.

*Primary Examiner*—Kent Bell
*Assistant Examiner*—June Hwu
(74) *Attorney, Agent, or Firm*—Greenlee Winner and Sullivan, PC

(57) ABSTRACT

*Hydrangea macrophylla* 'Blushing Bride' blooms on new growth without a cold requirement. It has rounded habit and glossy green, mildew-resistant leaves. The white mophead inflorescence matures to pale pink or light blue depending on the availability of aluminum in the soil.

5 Drawing Sheets

Botanical designation: *Hydrangea macrophylla* (Thumb.) Ser. 'Blushing Bride'.

BACKGROUND OF THE INVENTION

The present invention relates to a new and distinct cultivar of *Hydrangea macrophylla*, a member of the Hydrangeaceae family, hereinafter referred to by its cultivar name 'Blushing Bride'. This cultivar is grown primarily as an ornamental for landscape use and for use as a potted plant. The cultivar originated from controlled cross-pollination of *Hydrangea macrophylla* 'Veitchii' (unpatented) by *Hydrangea macrophylla* 'Bailmer' (U.S. Plant Pat. No. 15,298) at the University of Georgia, Athens, Ga. in 2001, and was selected from the progeny seedlings of this cross by continued evaluation for reblooming, increased resistance to mildew, and improved leaf and flower characteristics.

'Blushing Bride' has been asexually reproduced by softwood cuttings in Athens, Ga. since 2002. The characteristics of the cultivar have been stable and reproduced true to type in successive vegetative generations.

'Blushing Bride' is distinguished from its female parent 'Veitchii' by its reblooming trait, and from its male parent 'Bailmer' by flower color, leaf color, and increased resistance to mildew. 'Blushing Bride' has glossy, darker green leaves than 'Bailmer'. 'Blushing Bride' had no mildew in late summer and fall, whereas in side by side comparisons 'Bailmer' scored up to 25% mildew leaf infections. 'Blushing Bride' has white mophead inflorescences in both non-aluminum and aluminum media, which matured to pale pink and light blue respectively, whereas 'Bailmer' produces pink or blue mophead inflorescences respectively. The sterile florets of 'Blushing Bride' are mainly double, with two layers of sepals, providing a denser inflorescence than that of 'Bailmer' and most other mopheads which have simple florets. The leaves of 'Blushing Bride' develop yellow to red autumn color whereas leaves of 'Bailmer' senesce green to brown. There are no other reblooming cultivars of *Hydrangea macrophylla* with white mophead inflorescences known to the inventor.

SUMMARY OF THE INVENTION

'Blushing Bride' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'Blushing Bride' from all other varieties in commerce known to the inventor.

1) Remontant (reblooming) trait, flowering on old wood and new growth of the season from May to as late as October in Athens, Ga.
2) White mophead inflorescences, containing sterile florets many of which have double layers of sepals, maturing to pale pink or light blue in non-aluminum or aluminum based media respectively.
3) Rounded habit and strong stems.
4) Glossy dark green leaves.
5) Mildew resistant leaves. Plants of this cultivar have exhibited greater mildew resistance than other varieties of *Hydrangea macrophylla* known to the inventor.
6) Beautiful yellow to red fall color.

BRIEF DESCRIPTION OF DRAWINGS

The accompanying illustrations show characteristics of the new cultivar in photographs as true to color as is reasonably possible to make in illustrations of this nature.

BOTANICAL DESCRIPTION OF THE PLANT

Figure 1:
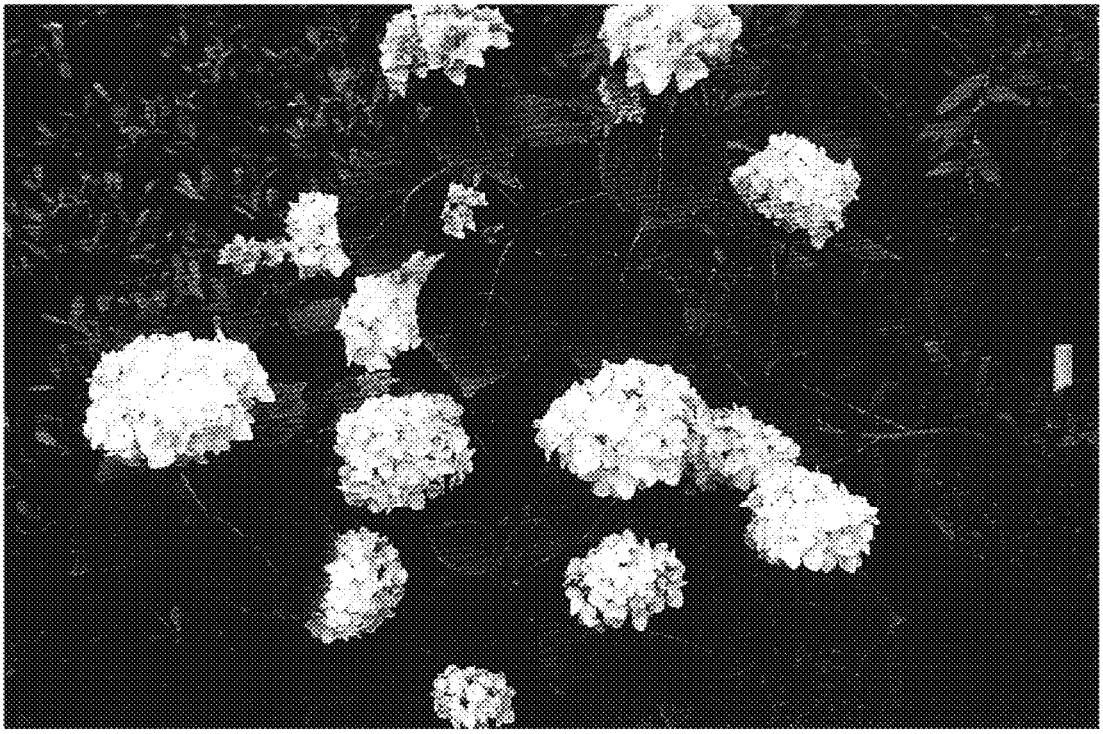
FIG. 1. A three-year-old plant growing in partial shade in a 27 liter container without aluminum, at Athens, Ga. May 17, 2003. The inflorescences are maturing to their pink color.
Figure 2:
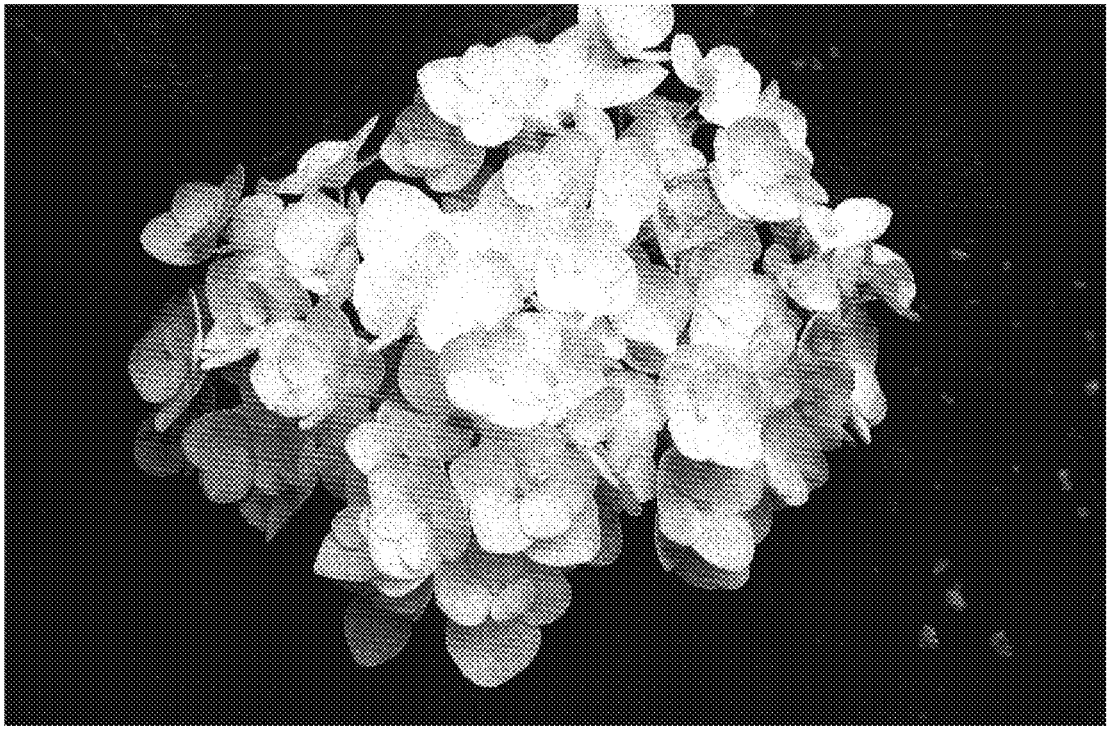
FIG. 2. Close up of peak flowering inflorescence of plant grown in absence of aluminum showing double sterile florets with the beginning of pale pink blushes.
Figure 3:
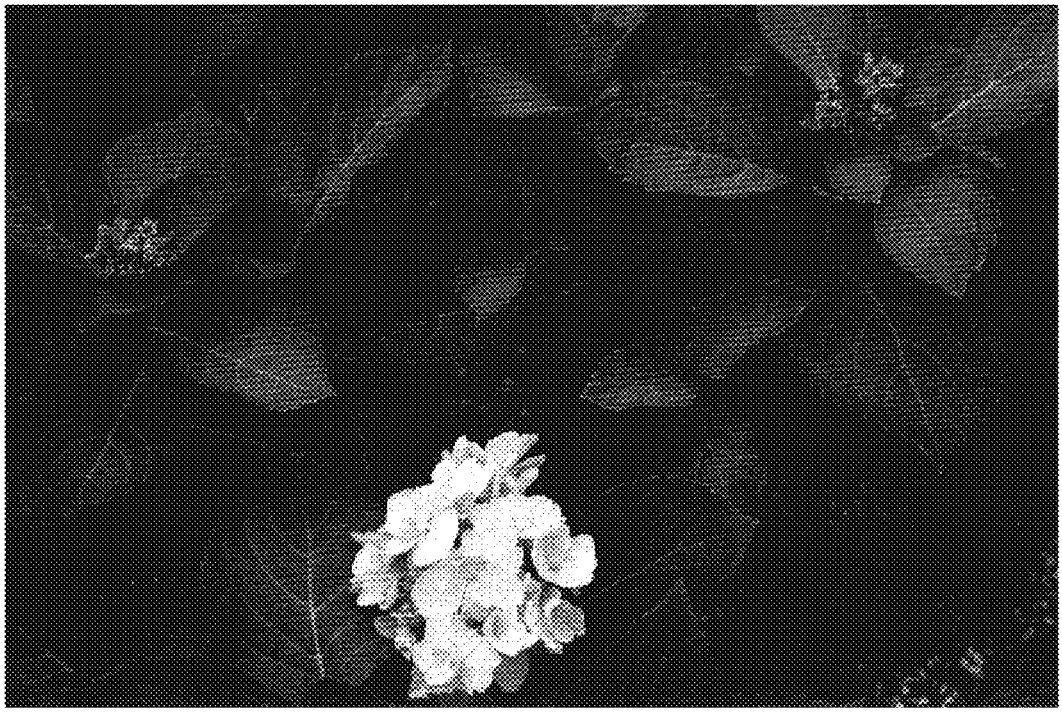
FIG. 3. Inflorescences developing on new growth of a three-year-old plant growing in the absence of aluminum. May 27, 2004.
Figure 4:
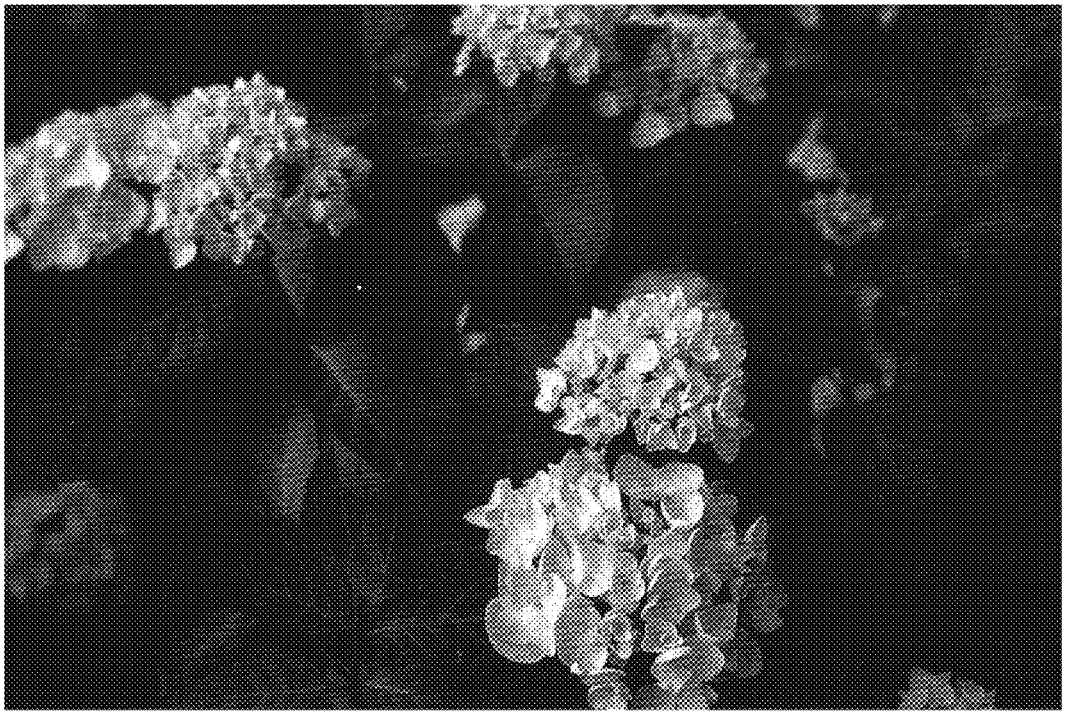
FIG. 4. Inflorescences maturing to light blue on plant growing in presence of aluminum.
Figure 5:
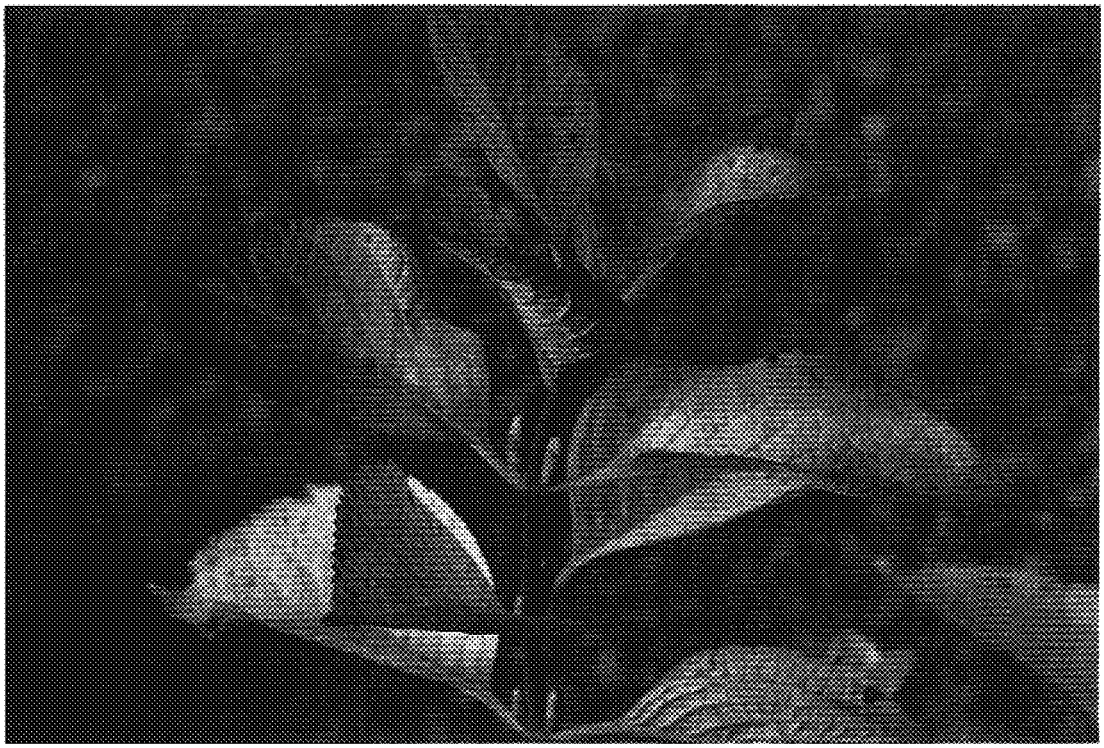
FIG. 5. Shoot showing development of fall colors, Dec. 2, 2004.

A detailed description of 'Blushing Bride' follows. Colors are based on The Royal Horticultural Society Colour Chart, 2001 edition. All measurements/characteristics were taken from two-year-old, 11.8 liter container grown plants, growing under 50% shade at Athens, Ga. (USDA Zone 7b) Measurements of leaves/stems and floral characteristics are the average of 10 to 20 samples, and were taken throughout the flowering period, from May through October in Athens, Ga. To determine the influence of aluminum on flower color, 0.75 ounces were added to the medium surface when inflorescences were visible, green, with cauliflower-shaped buds.

Classification:
- *Botanical.*—'Blushing Bride' is a cultivar of *Hydrangea macrophylla.*
- *Parentage.*—A progeny from a *Hydrangea macrophylla* 'Veitchii'×'Bailmer' controlled cross.
- *Propagation.*—Vegetatively by cuttings.

Plant:
- *Size.*—55 cm high, 70 cm wide, June, 2004.
- *Habit.*—Mounded deciduous shrub, multistemmed and compact.
- *Branching.*—Many breaks (shoots) from base of one-year plants, i.e., freely branching. Branches range in length from 12 to 35 cm.
- *Vigor.*—An unpruned rooted cutting transplanted in September 2003, filled an 11.8 liter container by July/August 2004, with 5 to 7 shoots, each terminated by a fully developed inflorescence.
- *Hardiness.*—USDA Zones 4 to 9.

Stems:

First year:
- *Diameter.*—6.8 mm.
- *Shape.*—Round.
- *Texture.*—Stout, glabrous, lustrous.
- *Pubescence.*—None.
- *Exfoliation.*—Flaky.
- *Internodes.*—Average, taken from middle of shoot, 8.6 cm.
- *Color.*—Grey-Brown 199D.

Second year:
- *Diameter.*—3 mm.
- *Color.*—Greyed-Orange 164D to Greyed-Orange 165C.

Vegetative buds:
- *Arrangement.*—Opposite.
- *Shape.*—Ovoid.
- *Size.*—7 mm in length, 3.5 mm in width.
- *Color.*—Greyed-Orange 165 A to 166D to 165 C.

Leaf:
- *Size.*—Average mature size taken from midpoint of first year stem, 9.2 cm in length and 6.9 cm in width.
- *Shape.*—Ovate, with acuminate apex, acute base and coarsely serrate margin.
- *Texture.*—Thick, leathery, with very waxy surfaces.
- *Color.*—Emerging leaves (March) Yellow-Green 144A upper surface and Yellow-Green 146 D lower surface; mature leaves (June/July), upper surface Green 139A, and lower surface Green 137C; fall leaves develop a range of colors from yellow to red, peaking early to mid November in Athens, Ga.
- *Venation.*—Pinnate, veins are Yellow-Green 144D in color.

Petiole:
- *Shape.*—Saucer shaped.
- *Size.*—1.25 cm in length and 3 mm in diameter, glabrous.
- *Color.*—Yellow-Green 144A.

Flower buds:
- *Size.*—3 mm in length, 3 mm in width, and 3 mm in depth.
- *Shape.*—Round.
- *Color.*—Violet-Blue 97B when grown with aluminum, and Red-Purple 65C when grown without aluminum.

Inflorescence:
- *Bloom period.*—May to October, Athens and Dearing, Ga. The plant carried 27 inflorescences in June. An inflorescence contained 40 to 60 individual fertile flowers.
- *Shape and size.*—Mophead, 12 cm in length, 14 cm in width, and 9 cm deep. The inflorescence lasts for about 16 weeks. The peduncle averages 10 mm in length, is finely pubescent and is Violet 85A with aluminum and Violet-Purple 73D without aluminum.

Sterile florets: Most contain a double layer of sepals, the outer layer, usually 3 or 4 in number, ranging from 10 to 20 mm in length, and 8 to 19 mm in width. The inner layer, usually 3 or 4 in number, range from 8 to 12 mm in length and in width.
- *Shape.*—Ovoid with rounded apex, acute base, and entire margin.
- *Texture.*—Smooth with no pubescence.
- *Color.*—The upper and lower surfaces of the emerging immature florets are White 155A and develop to White-pure (no specification in Colour Chart) at peak flowering. The sepals slowly develop blushes of light blue in the presence of aluminum or pale pink in the absence of aluminum, maturing to Violet-Blue 98D or Purple 75B plus Violet-Blue 91B respectively.

Fertile flowers:

Petals:
- *Size.*—5 petals per flower, 2 mm in length and 1 mm in width.
- *Shape.*—Ovoid, with acute apex, acute base, and entire margin.
- *Texture.*—Smooth with no pubescence.
- *Color.*—At peak of bloom the upper and lower surfaces of petals are Violet-Blue 98D with aluminum. When grown without aluminum the upper and lower surfaces of the petals are Red-Purple 72C with Violet-Blue 93C at base.

Sepals:
- *Size.*—5 sepals, 3 mm in length and 2 mm in width.
- *Shape.*—Ovoid, with acute apex, acute base, and entire margin.

*Texture.*—Smooth with no pubescence.

*Color.*—At peak of bloom, the upper and lower surfaces of sepals are Violet-Blue 98D with aluminum and Purple 75B with Violet-Blue 91B at base when grown without aluminum.

Pedicels:

*Size.*—4 mm in length.

*Texture.*—Finely pubescent.

*Color.*—Violet-Blue 98B with aluminum and Red-Purple 65D without aluminum.

Stamens:

*Number.*—8 to 10.

*Anthers.*—1 mm in length and 1 mm in width, Yellow-Green 145B in color with aluminum and Greyed-Red 182C in color without aluminum.

*Filaments.*—1 mm in length and 0.5 mm in width, Blue 101B in color with aluminum and Purple 75A without aluminum.

*Pollen.*—White in color.

Pistil: Superior, 3 mm in length and 1 mm in width, Violet-Blue 98D in color with aluminum and Red-Purple 69D without aluminum.

*Stigma.*—Typically 2, but sometimes 3 per pistil, often fused together, round in shape and Violet-Blue 98D in color with aluminum and Red-Purple 69D without aluminum.

*Style.*—1 mm in length and tubular in shape, Violet-Blue 98D in color with aluminum and Red-Purple 69D without aluminum.

Fruit: The capsule fruit is oval, 3 mm in length and 2 mm in width. The color during early ripening (June/July) is Green 143A and at maturity is Brown 200B. The number of fruit varies widely.

Seed: The seed are ovoid, 0.5 mm in length and 0.25 mm in width, Brown 200B.

Diseases: Excellent resistance to powdery mildew. No other pest or disease resistance/susceptibility has been observed.

I claim:

1. A new and distinct variety of *Hydrangea macrophylla* plant, substantially as herein described and illustrated.

* * * * *